United States Patent [19]
Bell et al.

[11] Patent Number: 6,147,029
[45] Date of Patent: Nov. 14, 2000

[54] DISSOLVABLE TABLET THAT AUTOMATICALLY DELIVERS NON-TOXIC ROOT INHIBITOR TO DRAIN PIPES

[76] Inventors: Adam Warwick Bell, 7504 SE. 19th Ave., Portland, Oreg. 97202; Peter James Stragnola, 1120 Lincoln Ave. #3, San Rafael, Calif. 94901

[21] Appl. No.: 09/114,870

[22] Filed: Jul. 14, 1998

[51] Int. Cl.[7] ........................... A01N 25/08; A01N 25/34
[52] U.S. Cl. ........................... 504/116.1; 504/358
[58] Field of Search ..................... 504/116, 358, 504/116.1

[56] References Cited

U.S. PATENT DOCUMENTS 3,231,398   1/1966   Pauli .......................... 106/16
5,116,414   5/1992   Burton et al. ................. 71/121

OTHER PUBLICATIONS

Devine et al. Physiology of Herbicide Action. Chapter 14: "Herbicides with Auxin Activity". p. 295–309, 1993.

*Primary Examiner*—S. Mark Clardy

[57] ABSTRACT

Methods and devices for cheaply, simply and efficiently keeping drains clear of roots involving the delivery of a root retardent hormone into drain pipes by incorporating the hormone into a tablet that is placed into a drainage system such as a toilet tank, thereby delivering the hormone to the drain pipes each time the toilet is flushed.

12 Claims, No Drawings

DISSOLVABLE TABLET THAT AUTOMATICALLY DELIVERS NON-TOXIC ROOT INHIBITOR TO DRAIN PIPES

FIELD OF INVENTION

The invention relates to methods and devices for keeping drains clear of roots, more specifically, to a device and method for delivery of a root retardent substance into drain pipes, most specifically, to a root hormone that can be incorporated into a tablet that is placed into a toilet tank, thereby delivering the hormone to the drain pipes each time the toilet is flushed.

BACKGROUND OF THE INVENTION

This invention relates to the prevention of root damage to underground drain pipes. It is well known in plumbing and home maintainance fields that roots cause considerable damage and inconvenience by damaging and invading underground drainage pipes. Domestic drainage pipes are commonly laid in a below-ground region shared with the roots of trees and shrubs. Pipes, over time, are subjected to tension, compression and sheer forces, due to ground shifting and due to expansion and contraction caused by changes in temperature. Frost and animals may cause damage, and in the case of metal pipes, especially iron pipes, electrophoretic effects lead to rusting, oxidation and decomposition. Pipes can be subjected to chemical attack from inside, such as from chemicals being flushed into a drain, for instance when caustic or acidic chemicals are poured down a drain to dislodge a clog such chemicals may remain behind the clog for a considerable time until the clog is dislodged. Damage to underground pipes increases with age of the pipes, and since the pipes are underground,often goes undetected until there is a serious problem.

Along with water, underground pipes frequently carry away domestic sewage which is high in nitrates, other minerals and organic compounds that stimulate root growth. These growth-stimulating compounds are very attractive to plants. Water, of course, is also needed by plants and as such, plant roots grow towards sources of water. Plant roots sense water and nutrient compounds at very small concentrations in the soil and will grow up a gradient of such compounds towards the source of the compounds. Even a tiny leak from a pipe is often sufficient to attract root growth. Such root growth is not random, but directional, and growing roots will seek out the source of the stimulating compound. Roots will grow towards any leak in a pipe, such as a loose joint or crack, and will grow into this place. The insinuating root grows both axially (lengthwise) and radially (in diameter) and as its girth expands it will cause further damage to the pipe, causing cracks and severe leaks that may eventually necessitate digging up the pipe to effect replacement or repair. Obviously such repair is expensive and inconvenient. Often, rather than breaking the pipe, the effect of root growth will be to block the pipe. This happens when roots invade the lumen of the pipe and, because of the high nutrient concentration, proliferate inside forming a mass of roots that can trap solid matter and quickly block the pipe. This, of course is advantageous to the plant, producing a mass of roots with large root surface area over which nutrients are absorbed, but is bad for the pipes and for the owner who must pay for repairs.

The prior art solutions to these problems have involved mechanical and chemical removal or roots, and when pipes have been damaged, digging up and replacing the pipes. Dealing first with damaged and leaking pipes, the only solution is excavation of the area, cutting back and destruction of the roots, and replacement of the pipes. Excavation is very costly, not least because the location of the damage is frequently not apparent until it has been uncovered, necessitating digging a trench along the path of the pipe until the point of damage has been found. Having found the damage, the roots must be cut back, necessitating further digging. If roots are to be destroyed, they may be poisoned, for instance by the injection of a powerful root poison directly into the root or the application of such a poison to the outside of the root. Such poisons often kill the entire tree or shrub, which is frequently undesirable, especially in the case of larger trees or shrubs, which when dead, require expensive removal and stump extraction.

Turning to the problem of pipes blocked by invading roots, the least expensive and inconvenient solution is often to treat the pipes with a substance that poisons and/or dissolves the roots. These substances, which may be poured down a drain or poured into a toilet, are frequently toxic to humans, other animals and to plants. The substances are usually in liquid form and are flushed into the drain where they contact the roots. Because these treatments require time to work, it is essential that the toilet or bath etc not be used for a certain amount of time, usually several hours. Apart from the inconvenience this causes, such directions are often not followed, making the treatment ineffective and a waste of time and money. This is especially so in the context of an apartment building or shared housing where many units share a common drain pipe; it can be hard to coordinate all tenants not to use the bathroom for several hours. The cost of these problems is well known to all apartment owners and managers.

Chemical treatments are only partially effective and often the root ball inside the pipe cannot be effectively removed by these methods. Roots are made of lignin which is tough and resilient to degradation. Even when dead, the roots may continue to block the pipe. Additional treatments are often administered, causing additional expense and additional pollution by pouring still more toxic substances down the drain, which leach out into the soil and may eventually reach ground-water, rivers and streams and potentially contaminating drinking water. Such additional treatments may be equally ineffective, leaving only one solution, mechanical removal. Certain chemical treatments have been designed to foam inside the pipe, thus filling the entire lumen of the pipe to effect better contact with both the upper surface and the lower surface of the pipe. Such foaming treatments, however, still have all the general disadvantages of chemical treatments, because, to work, they need to be concentrated upon the clogged area for several hours. Toxic treatments may adhere to the sides of drain pipes and so inhibit root growth, but this inhibition will last only until these substances are washed away, not providing effective deterrence of root growth.

Mechanical removal usually requires calling out the "rooter" company which uses a flexible snake which may have knives attached to the end to cut through roots. Cutting the roots removes them, at least partially, but does not prevent renewed root growth which may be very rapid, and it is therefore only a temporary solution. Also, mechanical removal does not repair the damaged pipes, nor does it prevent initial or further root growth into the pipes. All in all, mechanical removal may be a practical solution to an emergency problem of root-blocked pipes, but it is a temporary solution with no preventative qualities, and it is expensive.

There is a need for a treatment that cures the problem of root growth in underground drainage pipes and that prevents and deters root growth into pipes. There is a need for a substance to prevent root growth that is safe to use and is non-poisonous to humans, other animals and plants, and that is easily biodegradable. There is a need for a substance to prevent root growth that will not kill the entire plant from which the roots emanate. There is a need for a treatment that can be applied continuously and effectively, with the minimum of inconvenience. There is a need for such a treatment that is inexpensive. There is a need for such a treatment that can be used without requiring that bathrooms must not be used for the treatment period. There is a need for a hormonal treatment for pipes that prevents root invasion and growth wherein the hormone can be delivered automatically and simply each time a toilet is flushed.

SUMMARY OF THE INVENTION

The present invention is a device and a method for preventing roots from growing into an underground pipe and for stopping the further growth of roots that have already invaded an underground pipe. The present invention involves the delivery of a plant hormone into a drain pipe by placing a tablet containing the hormone inside a domestic toilet tank. Every time the toilet is flushed, hormone is delivered into the underground pipes at a concentration sufficient to deter root growth such that the hormone, at an appropriate concentration will (a) leak out of a leaking pipe into the surrounding soil to contact growing roots and (b) contact growing roots already within the pipe. The hormone so delivered controls root growth and when in contact with a root, will be absorbed by the root and will deter further root growth, either by (a) stopping or dramatically slowing further growth or (b) inducing shoot growth or the growth of other non-root tissue such as leaf or flower tissue. Non-root tissue so expressed will not be able to penetrate into pipes as would a root. Roots have evolved to be hardy, resilient, penetrative structures that seek out water and nutrients and grow towards them, but other structures, such as shoots and flowers and leaves have different qualities and "inappropriately expressed", will not have the destructive potential of roots. Such a hormone may act on the meristem of the root and affect cell growth and differentiation as well as taxis (directional growth) of the plant organ.

Hormones act at very low concentrations, so making it easy to minimize the amount of hormone of the invention needed to be delivered to the pipe or surrounding soil. Such hormones may act locally, meaning that delivery of the hormone to the growing underground root of a plant need not affect the other tissues or structures of the plant, meaning that the plant need not be killed or systemically harmed by the treatment, rather this is a "topical" treatment. Hormones are organic molecules and are naturally degraded in the environment and such a treatment will prevent root invasion without having to release large concentrations of dangerous or toxic or environmentally persistent chemicals into the soil.

The present invention cures the problem of root growth in underground drainage pipes by using hormones to prevent and deter root growth into pipes. The present invention is safe to use and, in quantities and concentrations typical to normal use, is not highly toxic or poisonous to humans or other animals and is easily biodegradable. The present invention will prevent destructive root growth but will not kill the entire plant from which the roots emanate. The present invention can be applied continuously and effectively, with the minimum of inconvenience. The present invention is inexpensive to practice and can be used without requiring that bathrooms must not be used for the treatment period. The present invention is a hormonal treatment for pipes that prevents root invasion and growth wherein the hormone can be delivered automatically and simply each time a toilet is flushed.

Other features and advantages of the invention will appear from the following description in which the preferred embodiments have been set forth in detail, in conjunction with the accompanying drawings (if any).

DESCRIPTION OF THE INVENTION

The present invention involves the delivery of a plant hormone into a drain pipe by placing a tablet containing the hormone inside a domestic toilet tank. Every time the toilet is flushed, hormone is delivered into the underground pipes to deter root growth such that the hormone, at an appropriate concentration, will (a) leak out of a leaking pipe into the surrounding soil to contact growing roots and (b) contact growing roots already within the pipe. The hormone so delivered controls root growth and when in contact with a root, will be absorbed by the root and will deter further root growth, either by (a) stopping or dramatically slowing further growth or (b) inducing shoot growth or the growth of other non-root tissue such as leaf or flower tissue. Non-root tissue so expressed will not be able to penetrate into pipes as would a root.

One embodiment of the present invention is a device to prevent root invasion of and growth in pipes, comprising a tablet containing a plant hormone, for example an auxin or tropin, eg: "auxin a" ($C_{18}H_{32}O_5$) or "auxin b" ($C18H30O4$) or heteroauxin ($C_{10}H_9O_2N$) or a tropin. (Other hormones or combinations of hormones may be used, those mentioned herein are mentioned by way of example only.)

Another embodiment of the invention is a method to prevent root growth and invasion into pipes that comprises providing the elements of the device disclosed herein and using these elements as described herein to prevent and deter root growth and invasion into pipes.

The substance used to prevent root growth and invasion may be a hormone, such as an auxin or tropin. Alternatively, the substance may be a hormone derived from an auxin or tropin.

As used herein, the term auxin shall be used to include any substance derived from an auxin, that is to say any substance either synthesized from and auxin or having a chemical structure that includes the chemical structure of an auxin. Similarly, as used herein, the term tropin shall be used to include any substance derived from a tropin, that is to say any substance either synthesized from a tropin or having a chemical structure that includes the chemical structure of a tropin.

Alternatively the substance used to prevent root growth and invasion may be a "hormone-like substance". As used herein, "hormone-like substance" means a substance other than a hormone that, none-the-less has hormone-like properties, i.e. that effects growth and/or differentiation in some way by acting on internal physiological signals that control growth and/or differentiation. For instance, a hormone or hormone-like substance may inhibit the action of endogenous plant hormones or may act as an "agonist" or "antagonist" to endogenous plant hormones, such as endogenous auxins or tropins, thereby inhibiting growth or inducing differentiation of growing tissue at the tip of a root into shoot tissue. In all embodiments of the invention where a hormone is used, a "hormone-like substance" may be used instead of or in conjunction with the hormone.

In a typical embodiment, the tablet is dropped into the cistern (the toilet tank containing water used for flushing) of a toilet and therein releases the hormone. Such a tablet may have a total mass of, for example, 0.1 grams to 1000 grams, and may contain from about 0.1 nanogram to about 100 grams of hormone. In other embodiments, the tablet will weigh from about 1 gram to about 100 grams, and contain from about 0.1 microgram to about 1 gram or hormone. For some embodiments, it would be advantageous for the tablet to weigh from about 2 grams to about 50 grams, and contain from about 0.1 microgram to about 10 micrograms of hormone.

Release of the hormone is at a semi-controlled rate, releasing the hormone little by little, over a period of time. The effective concentration of the hormone as delivered to the pipes and to the surrounding soil may be calculated by standard methods, calculating dilution due to addition of water and due to radial diffusion from the leaking pipe. The effective concentration of the hormone should be that which will effect root growth and/or differentiation to prevent or deter root invasion of the pipes. An effective concentration may be a concentration that will inhibit root growth or stimulate "inappropriate expression" of tissues such as shoots or buds under the ground.

An effective concentration for auxins may be, for instance, from about $10^{-8}$ molar to $10^{-1}$ molar, or about $10^{-7}$ molar to $10^{-1}$ molar, or about $10^{-6}$ molar to $10^{-1}$ molar, or about $10^{-5}$ molar to $10^{-1}$ molar or about $10^{-3}$ molar to $10^{-1}$ molar. At such concentration ranges, and above, auxins inhibit root growth and may promote shoot growth. For some applications, it may be advantageous to provide higher concentrations, greater than $10^{-1}$ molar, for instance 1 molar. Elongation of roots is believed to be promoted only by low concentrations of auxins, such as, for example, about $10^{-8}$ molar and below. Higher concentrations of auxins are beleived to promote shoot growth. From about $10^{-8}$ molar up to about $10^{-3}$ molar, auxins are thought to promote shoot growth. Above about $10^{-3}$ molar auxins are believed neither to promote shoot or root growth. Promotion of root and shoot growth may be effected by hormones other than auxins, but the concentrations of auxins or other hormones in the invention will, in any case, be effective to effect tissue growth and differentiation such that root growth within and into underground pipes is inhibited.

Exact concentrations may be easily determined by routein experimentation by (1) growing a number of plants hydroponically so as to produce roots, (2) making auxin solutions of varying concentrations from about $10^{-15}$ to 1 molar, (3) placing the roots of the plants such that they are immersed in the solutions of varying concentrations, (4) obsrevong growth. The experiment may equally be carried out by making gels, such as agar gels, containing various auxin concentrations. Auxins are mentioned here only by way of example, and any hormone may be equally used in such an experiment or in the invention.

Release of hormones may be by leaching out of the hormone from the tablet, or preferably by slow dissolution of the entire tablet. Flushing of the toilet changes and agitates the water in the cistern, promoting further dissolution and/or leaching out of the hormone. In this embodiment, the root hormone is delivered to the drain pipes with every flush of the toilet. The hormone will contact the inner surface of the underground pipe and, if a leak is present, will leak out into the surrounding soil. If roots are already present in the pipe, the hormone will directly contact such roots.

In an alternate embodiment a foaming agent, such as a surfactant, such as a soap, or a non-surfactant foaming agent, may be added to the tablet or container containing the hormone or added in a separate tablet or container such that the foaming agent is released into the cistern water and is delivered to the pipes whenever the toilet is flushed. Such a foaming agent foams within the underground pipes, promoting coating of the pipes, especially on the upper interior surface of the pipes.

In an alternate embodiment the hormone may be contained in a container that is not a tablet, but is a vessel containing the hormone, which vessel may be placed in the cistern, releasing the hormone over a period of time at a more or less steady rate, or releasing a quantity of hormone into the cistern in response to each flushing action. Such a release may be in response to the action of the toilet handel or plunger, or may be in response to the lowering and/or rising water level inside the cistern. In one such embodiment, the vessel may be a plastic vessel that is hung inside of the cistern with a hook, hooked over the edge of the cistern with the vessel itself hanging in the water of the cistern.

In an alternate embodiment the hormone may be impregnated into a non-soluble matrix from which it is released, either over a period of time at a more or less steady rate, or in response to each flushing action.

In an alternate embodiment, the hormone may be added to the drains manually, as needed.

Alternatively, the hormone may be placed, not within the tablet or matrix or container, but may be placed on the outside surface of such a support from which it may be released, as in other embodiments described herein.

In an alternate embodiment the hormone may be placed, as a tablet or in a matrix or container, inside a drain pipe or other part of the drainage system, and not in the toilet cistern as in the other embodiments.

In this application, the phrase "means for containment" (of a substance that affects the growth and/or differentiation of a plant cell) shall include all the means set out above, including a soluble tablet, a non-soluble matrix and a container made of any substance.

In this application "water drainage system" shall include all parts of a system of containers and pipes, including toilet cisterns, that are used to drain waste water away from a residence or business building or industrial building.

In this application, the word "growth" as applied to plant cells, includes increase in size of cells, increase in number of cells and differentiation of cells, for instance cells of meristem tissue, to form new tissues and organs, for instance shoots.

SUMMARY, RAMIFICATIONS AND SCOPE

Accordingly, it will be apparent that the invention will automatically counteract the invasion and growth of plant roots in pipes.

The invention provides a device and method for delivery of a plant hormone into a drain pipes by placing a tablet containing the hormone inside a domestic toilet tank or inside another part of the drainage system. Every time the toilet is flushed, or when water otherwise runs into the drain, hormone is delivered into the underground pipes to deter root growth such that the hormone, at an appropriate concentration, will (a) leak out of a leaking pipe into the surrounding soil to contact growing roots and (b) contact growing roots already within the pipe. The hormone so delivered controls root growth and when in contact with a root, will be absorbed by the root and will deter further root growth, either by (a) stopping or dramatically slowing further growth or (b) inducing shoot growth or the growth of other non-root tissue such as leaf or flower tissue. Non-root tissue so expressed will not be able to penetrate into pipes as would a root.

The specificities in the above description should not be construed to limit the scope of the invention, but rather as examples of possible preferred embodiments. Thus, since numerous modifications and alternate embodiments will readily occur to those skilled in the art, the scope of the invention should not be limited by the afore-mentioned illustrative embodiments, but should be determined by the appended claims and their equivalents.

What is claimed is:

1. A method for keeping underground pipes free of roots comprising: providing a substance that alters growth of plant cells wherein said substance is a naturally-occurring plant hormone, and providing a means for containment of said substance, placing said substance into said means for containment, and placing said means for containment containing said substance into a water drainage system having underground pipes, wherein said substance is gradually released into said water drainage system, whereby root growth in and around said pipes is altered.

2. The method of claim 1 wherein said means for containment is a tablet that dissolves over time containing said substance and wherein said means for containment containing said substance is placed in a toilet cistern wherein flushing of said toilet promotes the release of said substance into said underground pipes.

3. The method of claim 2 wherein said roots include roots within said underground pipe and roots without said underground pipe.

4. The method of claim 2 wherein said substance is selected from the group consisting of an auxin and a tropin.

5. The method of claim 2 wherein said substance is a substance that causes roots to differentiate into non-root tissue.

6. The method of claim 2 wherein said substance causes root growth to slow.

7. The method of claim 6 wherein said substance causes root growth to stop.

8. A device for deterring root growth into and within pipes comprising: a substance that alters growth of plant cells wherein said substance is a naturally-occurring plant hormone, said substance being incorporated into a means for containment selected from a group consisting of (i) a tablet that dissolves over time, (ii) a non-soluble matrix and (iii) a vessel, wherein said substance is contained in said means for containment is placed into a water drainage system to deter root growth onto and within the pipes.

9. The device of claim 8 wherein the substance is a hormone and wherein the means for containment is a tablet that dissolves over time and wherein the means for containment is placed in a toilet cistern such that said hormone is released into said pipes with every flush of the toilet.

10. The device of claim 9 wherein said substance is a substance that causes roots to differentiate into non-root tissue.

11. The device of claim 9 wherein said substance causes root growth to slow.

12. The device of claim 9 wherein said substance causes root growth to stop.

* * * * *